United States Patent [19]
Bronstein et al.

[11] Patent Number: 5,847,161
[45] Date of Patent: Dec. 8, 1998

[54] 1, 2 CHEMILUMINESCENT DIOXETANES OF IMPROVED PERFORMANCE

[75] Inventors: Irena Bronstein, Newton; Brooks Edwards, Cambridge, both of Mass.

[73] Assignee: Tropix, Inc., Bedford, Mass.

[21] Appl. No.: 874,408

[22] Filed: Jun. 13, 1997

Related U.S. Application Data

[62] Division of Ser. No. 547,372, Oct. 25, 1995, Pat. No. 5,679,803.

[51] Int. Cl.$^6$ .................... C07F 9/06; C07F 7/02; C07D 305/14
[52] U.S. Cl. ............ 549/220; 549/214; 549/330; 549/332; 549/333; 435/810; 536/4.1
[58] Field of Search .................. 549/214, 220, 549/330, 332, 333; 435/810; 536/4.1

[56] References Cited

U.S. PATENT DOCUMENTS

| | | | |
|---|---|---|---|
| 4,978,614 | 12/1990 | Bronstein | 435/21 |
| 5,424,194 | 6/1995 | Otagiri et al. | 435/7.9 |
| 5,652,093 | 7/1997 | Cubbage et al. | 435/5 |

*Primary Examiner*—Ba K. Trinh
*Attorney, Agent, or Firm*—Oblon, Spivak, McClelland, Maier & Neustadt, P.C.

[57] ABSTRACT

A new class of stable dioxetanes bears a polycyclic stabilizing group and aryloxy moiety, the oxygen atom of which is provided with a protective group which can be removed by an enzymatic or chemical trigger admixed with the dioxetane. The polycyclic stabilizing group is preferably spiroadamantane. The group further bears an alkoxy, aryloxy, aralkyloxy or cycloalkyloxy moiety which is partially or completely substituted with halogens, particularly fluorine and chlorine. Proper selection of electron active groups on the stabilizing moiety, the aryl group and the OR group yields enhanced enzyme kinetics, superior light intensity and excellent detection sensitivity in various assays.

3 Claims, No Drawings

1, 2 CHEMILUMINESCENT DIOXETANES OF IMPROVED PERFORMANCE

This is a Division of application Ser. No. 08/547,372, filed on Oct. 25, 1995 now U.S. Pat. No. 5,679,803.

BACKGROUND OF THE INVENTION

1. Field of the Invention

This invention pertains to 1,2 dioxetanes which are stable under ambient conditions, and can be caused to chemiluminesce by removal of a protecting group to leave an oxyanion, which decomposes with the release of light. The dioxetanes are typically stabilized by a tricycloalkyl moiety, which may be spiro-bound, and bear an aryl group to which is bound the protected oxygen atom and an electron active substituent. The dioxetanes of this invention also include a halogenated oxy substituent on the 2-carbon. The dioxetanes show improved performance, enhanced sensitivity, and are suitable for use in a wide variety of assays and other detection applications.

2. Background of the Prior Art

The assignee of the invention addressed herein, Tropix, Inc., has pioneered and commercialized chemiluminescent dioxetanes for use in a wide variety of applications, including immunoassays, nucleic acid assays, artificial lighting materials and the like. Additionally, Tropix has developed dioxetanes which can be used to detect the presence of enzymes, including proteases and other endogenous enzymes, and a variety of exogenous enzymes, such as alkaline phosphatase, widely used as a marker or label.

Such compounds, and their preparation in purified form, are the subject of U.S. Pat. No. 4,931,569. An early commercial compound of this type is 3-(2'-spiroadamantane)-4-methoxy-4-(3"-phosphoryloxy)-phenyl-1,2-dioxetane disodium salt, generally identified as AMPPD, and available from Tropix, Inc. of Bedford, Mass. A variety of assays have been identified for compounds of this type, including the multi-analyte assay of U.S. Pat. No. 4,931,223, also assigned to Tropix, Inc. Use of these compounds to generate a chemiluminescent signal which is easily detected, and/or quantified, can be improved by the incorporation in the assay of "enhancer" compositions, as is specifically addressed in U.S. Pat. No. 4,978,614 and extensively disclosed in U.S. Pat. No. 5,330,900, also commonly assigned herewith. Typically, these enhancement agents have a quaternary onium salt structure, such as poly(vinylbenzyltributylammonium chloride) and poly(vinylbenzyl tributylphosphonium chloride) as well as the corresponding phosphonium and sulfonium salts and can form hydrophobic regions or areas within an aqueous environment, to enhance chemiluminescence.

Commercially developed dioxetanes can be generally represented by the structural Formula:

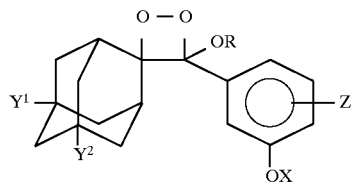

As noted, among the "first generation" dioxetanes commercially developed, $Y^1$, $Y^2$, and Z are hydrogen, and R is a methyl group. In AMPPD, X is a phosphate group, while other "first generation" dioxetanes have also been developed and disclosed, wherein X is a different group which can be cleaved by an enzyme. Potential identities for X are well known, and include as well as phosphate, acetate, various galactosides and glucuronides and in general, any group susceptible to cleavage by an enzyme. Representative identities are set forth in Table 1 of U.S. Pat. No. 4,978,614, identified as Group Z. "Second generation" dioxetanes have been developed, disclosed and patented, wherein one or more of $Y^1$ and/or $Y^2$ of the above general Formula I have identities other than hydrogen, so as to improve chemiluminescence intensity, chemiluminescence kinetics, or both. Compounds of this type bear an active substituent on the spiroadamantyl group, that is, at least one of $Y^1$ or $Y^2$ is a group other than hydrogen. In an embodiment characteristic of this "second generation" either bridgehead carbon bears a chlorine substituent (CSPD). A wide variety of other active substituents are set forth in U.S. Pat. No. 5,112,960 and other patents assigned to Tropix, Inc. Instead of a chlorine substituent, the adamantyl ring may bear a methylene substituent, as recited in claim 1 of U.S. Pat. No. 5,326,882, to Tropix, Inc. The importance of control over enzyme kinetics (including $T_{1/2}$), light intensity and detection sensitivity are stressed in U.S. Pat. No. 5,112,960.

U.S. Pat. No. 5,326,882 also discloses and claims "third generation" tri-substituted phenyl compounds, that is, dioxetanes of the structure set forth above, wherein each of $Y^1$ and $Y^2$ may be either hydrogen or an active group, and the phenyl ring bears in addition to the enzyme cleavable group linked to the phenyl through an oxygen atom, an electron active substituent which influences enzyme kinetics and/or chemiluminescence intensity. This electron active group, Z in the above Formula, can either retard or accelerate the chemiluminescence obtained. Chemiluminescence is produced after the cleavage of the enzyme-cleavable X group of general Formula I by admixing or combining a suitable dioxetane with a corresponding enzyme specific for the X moiety. This can be accomplished in an aqueous sample, as discussed above, or on a membrane or other solid support. Membranes and similar solid supports can be optimized for increased chemiluminescent signal intensity and sensitivity of detection, by providing a polymeric membrane as disclosed in U.S. Pat. No. 5,336,596 to Tropix, Inc.

The dioxetanes described above are specifically prepared for use in connection with enzymatic assays. Thus, the X substituent, whose removal induces decomposition and chemiluminescence, is specifically designed to be removed by an enzyme. The enzyme may be the target analyte in the sample inspected, or it may be a reporter molecule attached to a probe, antigen or antibody, or any member of a specific binding pair, to detect the presence of the other member of the specific binding pair. Assay formats of this type are well known, the dioxetane chemiluminescence allowing the assay to be improved such that highly efficient, precise and sensitive detection of specific targets can be achieved.

It is also possible to select X such that it is not susceptible to removal by an enzyme, but can be removed by a specific family of chemicals. U.S. Pat. No. 4,956,477 describes various synthesis methods to prepare a wide family of dioxetanes of general Formula 1, wherein X can either be an enzyme-cleavable group, or a chemically cleavable group, such as a hydrogen atom, an alkanoyl or aroylester, an alkyl or aryl silyloxy or similar groups. Compounds of this type are also described in U.S. Pat. No. 4,962,192, Schaap, wherein the moiety X of general Formula I can be either cleavable by an enzyme or removed by a chemical. In its simplest form, X is hydrogen, whose departure can be triggered by a wide variety of "activating agents", among the simplest of which is sodium hydroxide. Because the decomposition reaction produced by the removal of the cleaving group X produces light through the decomposition of O—O bond of the dioxetane ring, to produce two carbonyl-based compounds, where the activating group is a chemical, only one photon of light can be produced per molecule of activating agent. This should be contrasted with the enzyme-triggerable dioxetanes discussed above, wherein the enzyme, as a catalyst, triggers the decomposition of many dioxetane molecules present as substrates. This catalytic multiplying effect has led to the commercial development and acceptance of enzyme-triggerable dioxetanes. Advanced chemically (non-enzymatically) triggerable dioxetanes are the subject of U.S. patent application (not yet assigned), filed as Attorney Docket No. 4085-097-27, on Oct. 19, 1995.

Accordingly, it remains an object of those of skill in the art to obtain dioxetanes which give adequate chemiluminescence, with appropriate emission kinetics, and which are triggerable by activating agents including enzymes and non-enzymatic chemicals, such that they can be used in assays wherein high light intensity, improved enzyme kinetics, and high sensitivity are requirements.

SUMMARY OF THE INVENTION

The above objects, and others made clear by the discussion set forth below, is met by a new family of dioxetanes which can be triggered to decompose and chemiluminesce by either enzymatic triggering agents or chemical triggering agents, depending on the identity of the protective group, which dioxetanes, by virtue of the substituents selected on the stabilizing and aryl groups, together with the provision of a halo-substituted alkoxy moiety on the 2-carbon of the dioxetane, exhibit enhanced sensitivity, enzyme kinetics and light intensity.

The dioxetanes are of the general formula II set forth below.

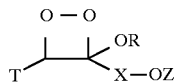
                                                    II

T is a polycycloalkyl dioxetane, preferably adamantyl dioxetane and most preferably spiroadamantane. X is phenyl or aryl. The aryl moiety bears, in addition to the group OZ, 1–3 electron active groups, such as chlorine or methoxy, as described in U.S. patent application Ser. No. 08/231,673 filed Apr. 25, 1994. The entire disclosure thereof is incorporated herein by reference. Z is a protecting group which can be removed either by an enzyme, such as a phosphate group removed by a phosphatase, or a protecting group removed by a chemical triggering agent, such as hydrogen, or substituted silyl moieties, which can be removed by the addition of a base. Moiety R is of 1–20 carbon atoms, and an alkyl, aryl, aralkyl or cycloalkyl, each of which may include 1–2 heteroatoms which may be P, N, O or S which group R is halogenated. Most preferably, R is a trihaloalkyl moiety.

When X is naphthyl, OZ is at a point of attachment, preferably, to the naphthyl ring, in relation to the ring's point of attachment to the dioxetane ring, such that the total number of ring atoms separating these points of attachment, including the ring atoms at the points of attachment, is an odd whole number, in a fashion analogous to the substitution pattern disclosed in U.S. Pat. No. 4,952,707.

The polyciclic group T can be substituted with an electron active group, including electron donating and electron withdrawing groups, or may be unsubstituted. Preferred substituents include hydroxyl, halo (preferably F and Cl) and alkyl. Preferred identities for R include fluorinated alkyls, aryls, cycloalkyls or cycloaryls, including heteroalkyls, wherein the carbons are partially or fully substituted with fluorine or chlorine atoms.

Dioxetanes of this structure can be used to detect the presence of the triggering agent, such as an enzyme or a base, used in immunoassays in the fashion disclosed in U.S. Pat. No. 5,112,960, which is incorporated herein by reference, in nucleic acid probes, in the fashion disclosed in U.S. Pat. No. 5,326,882, which is incorporated herein by reference, either alone, or in conjunction with enhancement agents, such as those disclosed in U.S. Pat. No. 4,978,614, which is also incorporated herein by reference.

The present invention is also directed to a kit comprising a dioxetane of the general formula II and a triggering agent which removes Z when admixed with the dioxetane in an aqueous environment. Z can be an enzymatically cleavable or a non-enzymatically cleavable group. When Z is enzymatically cleavable the triggering agent is an enzyme which is capable of cleaving group Z. When Z is non-enzymatically cleavable the triggering agent is a base.

DETAILED DESCRIPTION OF THE INVENTION

The dioxetanes of this invention, having the general formula II

                                                    II show improved light intensity, enzyme kinetics, and/or sensitivity, depending on the particular identities of the substituent selected.

Substituent T is principally selected as a stabilizing moiety. Dioxetanes without such stabilizing moieties spontaneously decompose, or decompose under mildly elevated thermal conditions. A polycyclic moiety, such as an adamantyl group, lends stability to the overall dioxetane. In preferred embodiments, T is spiroadamantane. Either bridgehead carbon, or both, may bear electroactive substituents, which may affect enzyme kinetics and light intensity. Each bridgehead carbon (5 and 7 positions on the adamant-2-ylidene substituent) can be, independently, hydrogen, a hydroxyl group, a halo substituent, particularly fluoro or chloro, an unsubstituted straight or branched chain lower alkyl group of 1–6 carbon atoms, a lower alkyl group mono- or di-substituted with a hydroxy, 1–3 halogens or similar substituent, a phenyl group, unsubstituted or substituted with halogen or lower alkoxy substituents, a cyano group, an amide group, and other substituents which are either electron donating or electron withdrawing.

X in general formula II is either phenyl or naphthyl, substituted with 1–3 groups A, which are independently selected from a wide variety of identities which are electron active substituents. The essential characteristic of the A substituents on the phenyl or naphthyl moiety is that it does not suppress the chemiluminescent behavior of the dioxetane, although it may alter the emission kinetics. Preferred electron-active substituents include chloro, alkoxy (—OR), aryloxy (—OAr), trialkylammonium (—NR$_3$+), alkylamido (—NHCOR, —NRCOR'), arylamido (—NHCOAr, —NRCOAr, —NArCOAr), arylcarbamoyl (—NHCOOAr, —NRCOOAr), alkylcarbamoyl (—NHCOOR, —NRCOOR'), cyano (—CN), nitro (—NO$_2$), ester (—COOR, —COOAr), alkyl- or arylsulfonamido (—NHSO$_2$R, —NHSO$_2$Ar), trifluoromethyl (—CF$_3$), aryl (—Ar), alkyl (—R), trialkyl-, triaryl-, or alkylarylsilyl (—SiR$_3$, SiAr$_3$, —SiArR$_2$), alkyl- or arylamidosulfonyl (—SO$_2$NHCOR, —SO$_2$NHCOAr), alkyl or aryl sulfonyl (—SO$_2$R, SO$_2$Ar) alkyl- or arylthioethers (—SR, SAr). The size of the Z substituent is generally limited only by solubility concerns. Where reference is made to alkyl or R, R', etc., the alkyl moiety should have 1–12 carbon atoms. Suitable aryl moieties include phenyl and naphthyl as exemplary moieties. Particularly preferred species include chloro and alkoxy.

The stable dioxetanes of this invention are caused to chemiluminesce by deprotection of the phenoxy or naphthyloxy group, by removal of group Z. Z may be either a protective group removable by addition of a base or salt, or an enzyme-cleavable moiety. Thus, Z may be H or E$_3$Si, wherein E is independently hydrogen, alkyl, aryl or arylalkyl, each of 1–12 carbon atoms. Alternatively Z may be an enzyme-cleavable moiety. Thus, upon proper contact with a suitable enzyme, Z is cleaved from the molecule, leaving the oxygen attached to the phenyl ring, and thus, the phenoxy anion. Z may be phosphate, galactoside, acetate, 1-phospho-2,3-diacylglyceride, 1-thio-D-glucoside, adenosine triphosphate, adenosine diphosphate, adenosine monophosphate, adenosine, α-D-glucoside, β-D-glucoside, β-D-glucuronide, α-D-mannoside, β-D-mannoside, β-D-fructofuranoside, β-glucosiduronate, P-toluenesulfonyl-L-arginine ester, P-toluenesulfonyl-L-arginine amide, phosphoryl choline, phosphoryl inositol, phosphoryl ethanolamine, phosphoryl serine, diacylglycerol phosphate diester and monoacylglycerol phosphate diester. The phosphoryl and phosphate ester moieties may be cleaved by, e.g., a phospholipase, generating a phosphate group, which may be cleaved by a phosphatase. Z, if an enzyme, is preferably phosphate, galactoside or glucuronide, most preferably phosphate. Preferably, when substituted on the phenyl ring, OZ is meta with respect to the point of attachment to the dioxetane ring, that is, it occupies the three position.

Group R is a straight or branched alkyl, aryl, cycloalkyl or arylalkyl of 1–20 carbon atoms. R may include 1 or 2 heteroatoms which may be P, N, S or O. The substituent R is halogenated. The degree of halogenation will vary depending on the selection of substituents on the adamantyl group, on the aryl group, and the desired enzyme kinetics for the particular application envisioned. Preferred groups include trihalo lower alkyls, including trifluoroethyl, trifluoropropyl, heptafluoro butyrol, hexafluoro-2-propyl, α-trifluoromethyl benzyl, α-trifluoromethyl ethyl and difluorochloro butyl moieties. The carbon atoms of substituent R may be partially or fully substituted with halogens. When R is aryl preferred groups may include a phenyl ring substituted with one or more chloro, fluoro, or trifluoromethyl groups, e.g. 2,5-dichlorophenyl, 2,4-difluorophenyl, 2,3,5,-trifluorophenyl, 2-chloro-4-fluorophenyl or 3-trifluoromethyl phenyl. Fluorine and chlorine are particularly preferred substituents, although bromine and iodine may be employed in special circumstances.

The halogen atoms, being particularly powerful electron withdrawing groups, are involved in several different types of interactions on the adamantyl, aryl and R substituents. Additionally, polyhaloalkyl groups are well known solubilizing agents. Thus, selection of the degree and type of halogenation on the R group will be made based on the identities and the presence of halogens on the adamantyl and aryl group, as well as the desired characteristics for the dioxetane.

One particularly preferred dioxetane within the scope of this invention is

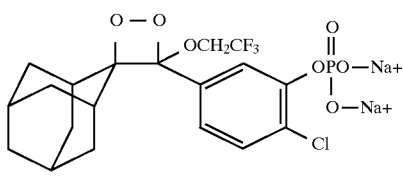

Other compounds, for purposes of demonstration of the invention, bearing similar structures have been prepared. Some of these, bearing the designation "star" fall within the scope of this invention. Comparative compounds, including CSPD, and TFE, have been presented for purposes of comparison. CSPD is the subject of the U.S. Pat. No. 5,112,960. TFE is addressed in commonly owned U.S. patent application Ser. No. 08/339,085. These compounds do not constitute part of the invention, but are included for the purposes of comparison.

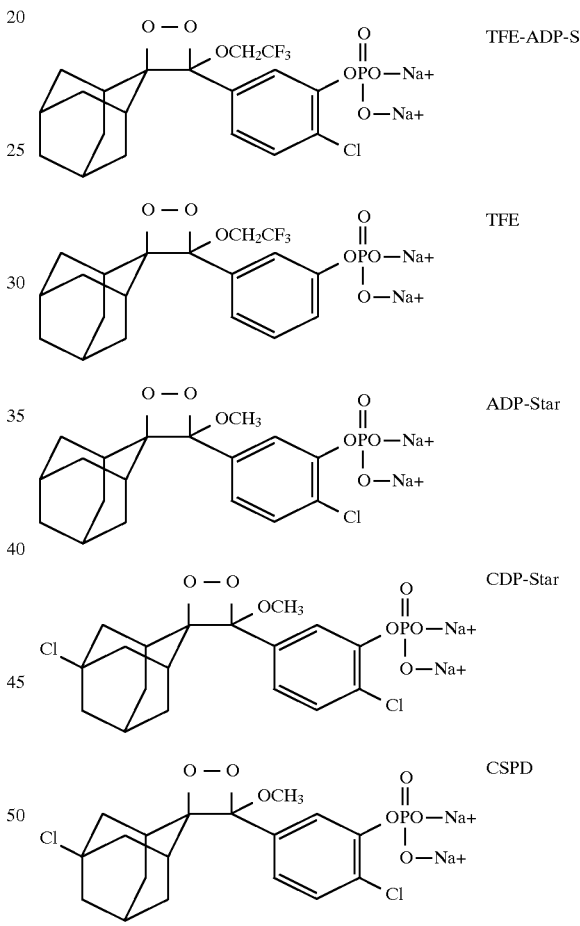

TFE-ADP-Star may be made by the following synthesis. 4-chloro-3-methoxybenzoyl chloride 4-chloro-3-methoxybenzoic acid, 3.7 g, was wet down with chloroform, 3 mL, and thionyl chloride, 6 mL, was added under an argon atmosphere. The resulting paste was subjected to reflux. After several minutes, the light yellow solution was cooled to room temperature and another 4.0 g of the substituted benzoic acid was added. The mixture was again brought to reflux for one hour. A still head was added to the flask in order to distill off chloroform and excess thionyl chloride at the minimum temperature possible. The still pot residue, containing the product, then solidified.

Petroleum ether, 5 mL, was added to dissolve the solid with slight heating. Upon cooling to room temperature, the mother liquor was pipetted off gently, and the remaining solid was pumped in vacuo to obtain 7.3 grams of 4-chloro-3-methoxybenzoyl chloride as a light tan solid. Another 1.03 grams of less pure material could be obtained from the mother liquor.

2,2,2-Trifluoroethyl 4-chloro-3-methoxybenzoate 4-chloro-3-methoxybenzoyl chloride, 2.3 g (11.2 mmol), was weighed out into a round-bottom flask under argon. Methylene chloride dried over 3 A molecular sieves, 20 mL, was added, followed by trifluoroethanol, 0.9 mL. The solution was stirred under argon in a water bath at 10° C. during the dropwise addition of triethylamine, 1.7 mL. Upon warming to room temperature, the slurry was stirred for one hour. Water, 20 mL, and methylene chloride, 10 mL, were added to the flask. The mixture was transferred to a separatory funnel, rinsing the reaction flask with methylene chloride. The lower organic layer was removed. The aqueous layer was extracted with methylene chloride, 10 mL. The combined organics were washed several times with water, passed through cotton and rotary-evaporated to an oil which solidified to yield 2.55 g. of a light tan product. TLC of the solid exhibited one spot (K5F $SiO_2$/methylene chloride:hexanes, 1:1) with an Rf value of 0.68. The infrared spectrum showed C=O (ester)stretch at 1737 $cm^{-1}$.

2-Chloro-5-(2,2,2-trifluoroethoxy-tricyclo[$3.3.1.1^{3,7}$]dec-2-ylidenemethyl) anisole Titanium trichloride, 7.9 g (51.3 mmol), was weighed into a round-bottomed flask in a glove bag under an argon atmosphere. Freshly distilled tetrahydrofuran (from LAH), 60 mL, was added quickly under argon flow. Care should be taken, as this addition can be exothermic. The purple suspension was stirred vigorously so as to break up the solid adhering to the walls of the flask. After 15 minutes, zinc dust, 5.2 g, was added all at once under argon with continued stirring. A moderate exotherm resulted in a reddish-brown mixture which did not contain black suspended solids. After 15 minutes stirring, the triethylamine, 11 mL, was added with exclusion of air. The mixture was then refluxed for 2 hours. A solution of 2-adamantanone, 3.0 g (20 mmol), and 2,2,2-trifluoroethyl-4-chloro-3-methoxybenzoate, 2.6 g (10 mmol) in dry THF, 30 mL, was added dropwise to the refluxing brown mixture over approximately 65 minutes. Reflux was continued overnight for 16 hours. The solvents were rotary evaporated from the cooled reaction mixture to yield a brown-black gum. This gum was triturated with hexanes, 100 mL, and ethyl acetate, 20 mL. The yellow-orange supernate was decanted and the trituration procedure was repeated. After 10 minutes of agitation, triethylamine and methanol, 5 mL each, were added. The gum began to stiffen and eventually became a lumpy solid. The solid was broken up and the supernate decanted. One final trituration was accomplished with 20% ethyl acetate-hexanes. The combined decanted supernates were rotary evaporated to a light yellow, semisolid paste. The mixture was treated with hot hexanes, 50 mL, and filtered warm to remove some insolubles. The residue obtained after rotary evaporation of the filtrate was applied to a 2.1×20 cm column of activity I aluminum oxide as a slurry in a small amount of warm hexanes. The column was eluted with hexanes to obtain adamantylidene adamantane. The elution was continued with 10% dichloromethane-hexanes to obtain an oil which contained two major mid Rf, UV-active components. The oil was taken up in a small amount of hot hexanes. A crystalline, colorless solid, weighing 0.71 g and having a melting point of 108°–112° C., precipitated out upon cooling.

I.R. ($CH_2Cl_2$): 2920, 2850, 1590, 1572, 1485, 1465, 1450, 1400, 1203, 1160, 1100, 1065, 1035, 993, 965, 870, 828 $cm^{-1}$.

$^1$H NMR (400 MHz-$CDCl_3$): δ 1.75–1.96(m, 14H) 2.60(s, 1H); 3.27(s, 1H); 3.70–3.76 (m, 2H-$CH_2CF_3$); 6.80–6.89(m, 2H); 7.31–7.33(m, 1H).

2-Chloro-5-(2,2,2-trifluoroethoxy tricyclo[$3.3.1.1^{3,7}$]dec-2-ylidenemethyl) phenol Sodium hydride (60% in mineral oil), 0.12 g, was washed three times with hexanes under an argon atmosphere. DMF, 6 mL, was added, and the slurry was cooled to 0° C. in an ice bath. With magnetic stirring, ethanethiol, 0.206 mL, was added dropwise with evolution of hydrogen gas. The mixture was then allowed to warm to room temperature over 15 minutes. 2-Chloro-5-(2,2,2-trifluoroethoxy tricyclo[$3.3.1.1^{3,7}$] dec-2-ylidenemethyl) anisole, 0.70 g, was added as a solid under argon flow. The flask was placed in an oil bath at 120° C. and stirred for one hour. The cooled mixture was then diluted with ethyl acetate:hexanes (1:1), 20 mL. An equal volume of aqueous 1M $NH_4Cl$ was added with vigorous swirling. The biphase was transferred to a separatory funnel where the organic layer was extracted again with 20 mL 0.5M $NH_4Cl$ solution, and then twice with 20 mL volumes of water. The organic layer was dried over $Na_2SO_4$ and pumped in vacuo to an oily product. TLC showed a single UV-active spot at Rf 0.56 (K5F; methylene chloride:hexanes, 1:1).

IR(neat): 3540 (OH), 3455 (OH), 2910, 2850, 1600, 1570, 1482, 1447, 1410, 1280, 1100, 1052, 996, 887, 855, 823, 800, 732 $cm^{-1}$.

Disodium 2-Chloro-5-(2,2,2-trifluoroethoxy-tricyclo [$3.3.1.1^{3,7}$]dec-2-ylidenemethyl) phenyl phosphate 2-Chloro-5-(2,2,2-trifluoroethoxy tricyclo[$3.3.1.1^{3,7}$]dec-2-ylidenemethyl) phenol, 490 mg (1.31 mmol), was dissolved in 10 mL dry THF. Triethylamine, 238 microliters, was added dropwise by syringe under argon. The solution was cooled in an ice bath for the dropwise addition of 2-chloro-2-oxo-1,3,2-dioxaphospholane, 143 microliters. The slurry was warmed to room temperature and stirred for 3 hours. The supernate was removed from triethylamine hydrochloride using a cotton-tipped syringe under argon flow. The solid was washed with two aliquots of dry THF, 5.0 mL each. The solvent was stripped from the combined filtrate to give a straw-colored gum. This was taken up in dry DMF, 4.0 mL, and treated with dry NaCN, 0.077 g, under argon. The mixture was allowed to stir overnight at room temperature. The solvent was stripped in vacuo at 50°–55° C. The orange gum obtained was dissolved in anhydrous methanol, 5.0 mL, and treated dropwise with a methanolic solution (4.3M) of sodium methoxide, 320 microliters. After stirring for 45 minutes at room temperature, a sample was removed for analytical HPLC on a Polymer Laboratories PLRS-S polystyrene, reverse-phase column. A gradient of acetonitrile, running against 0.1% sodium bicarbonate showed the product eluting at 12.24 minutes. The methanol was removed from the reaction mixture and the residue was dissolved in water, 50 mL. This solution was filtered and preparatively purified with two injections onto a large, one inch PLRP-S column. An acetonitrile/water gradient was applied which allowed the major product to be collected in two separate fractions. These were combined and lyophilized to yield a slightly off-white, fluffy solid weighing 517 mg.

$^1$H NMR ($D_2O$): δ 1.79–1.96 (m, 14H); 2.65 (s, 1H); 3.22 (s, 1H); 4.01–4.08 (m, 2H); 7.02–7.04 (m, 1H); 7.45–7.50 (m, 2H). This data supports the structure.

Disodium 2-chloro-5-(4-(2,2,2-trifluoroethoxy)spiro{1,2-dioxetane-3,2'-tricyclo[$3.3.1.1^{3,7}$]decan}-4-yl-phenyl phosphate (TFE-ADP-Star)

480 milligrams of chromatographed disodium 2-chloro-5-(2,2,2-trifluoroethoxy tricyclo[(3.3.1.1$^{3,7}$]dec-2-ylidenemethyl)phenyl phosphate was placed in a tube and wet down with anhydrous methanol, 4 mL. Chloroform, 40 mL, was added to obtain a solution. A solution of tetraphenylporphine (TPP), 6 milligrams in 3 mL chloroform, was then added to yield a pink-purple reaction mixture. The solution was cooled in an ice bath while sparging with oxygen through a Pasteur pipette for 5 minutes. The gas flow was continued while the solution was irradiated with a 400 watt sodium vapor lamp which had been filtered with a 3.0 mil thickness of DuPont Kapton film. After 40 minutes, a small sample was blown down and dissolved in water which contained 0.1% $NaHCO_3$. Analytical HPLC, under conditions described above for the starting material, indicated a new product which eluted at 12.1 minutes. The starting material, eluting at 12.5 minutes, was present in just a trace amount. The reaction was stripped of solvents and pumped to yield a dark red foam. This was dissolved in 80 mL water which contained 5 drops of 0.5M NaOH. The solution was filtered to remove insolubles, and was preparatively chromatographed on a one inch PLRP-S column (Polymer Laboratories) using an acetonitrile/water gradient. The product peak was shaved on the front and in the back, collecting only the middle cut. This eluant was freeze dried to obtain 293 milligrams of the product as a white solid. That the product was the entitled 1,2-dioxetane, was confirmed by enzymatic triggering of the material with alkaline phosphatase to produce light.

$^1$H NMR (400 MHz, $D_2O$): δ 0.87–0.90 (d, 1H); 1.17–1.20 (d, 1H); 1.20–1.71 (m, 10H); 2.17(s, 1H); 2.86 (s, 1H); 3.83 (br.m, 2H); 7.11 (br.m, 1 H); 7.38–7.40 (m, 1H); 7.68(br.m, 1H). This data supports the compound structure.

TFE-CDP-Star may be made by the following synthesis.

2-Chloro-5-2,2,2-trifluoroethoxy-(5'-chlorotricyclo [3.3.1.1$^{3,7}$]dec-2-ylidenemethyl) anisole Titanium trichloride, 10.1 g (65.6 mmol), was weighed into a round-bottomed flask in a glove bag under an argon atmosphere. Freshly distilled tetrahydrofuran (from LAH), 70 mL, was added quickly under argon flow. (Care should be taken, as this addition can be exothermic.) The purple suspension was stirred vigorously so as to break up the solid material adhering to the walls of the flask. After 15 minutes, zinc dust, 7.1 g, was added all at once under argon with continued stirring. A moderate exotherm resulted in a reddish-brown mixture which did not contain black suspended solids. After 20 minutes stirring, the mixture was cooled in an ice bath and several drops of triethylamine were added with exclusion of air. After an exotherm, an additional 12 ml N(Et)$_3$ was added. The mixture was then refluxed for 2 hours. A solution of 5-chloro-2-adamantanone, 3.7 g (20 mmol), and 2,2,2-trifluoroethyl 4-chloro-3-methoxybenzoate, 2.6 g (10 mmol) in dry THF, 40 mL, was added dropwise to the refluxing brown mixture over approximately 35 minutes. Reflux was continued for 2.5 hours whereupon TLC showed unreacted ester starting material. An additional 1.10 g of the chloro-adamantanone was added as a solid under argon flow. After another 2.5 hours of reflux, the cooled reaction mixture was stirred overnight at room temperature. The solvents were rotary evaporated from the cooled reaction mixture to yield a brown-black gum. This gum was triturated with hexanes, 100 mL, and ethyl acetate, 20 mL. The yellow-orange supernate was decanted and the trituration procedure was repeated. After 10 minutes of agitation, triethylamine and methanol, 2 mL each, were added. The gum began to stiffen and eventually became a lumpy solid. The solid was broken up and the supernate decanted. One final trituration was accomplished with 5% ethyl acetate-hexanes. The combined decanted supernates were rotary evaporated to a light yellow oil. The residue obtained after rotary evaporation of the filtrate was applied to a 2.1×20 cm. column of silica gel. The column was eluted with 5 to 10% ethyl acetate in hexanes to five fractions which contained a mid Rf UV-active spot, contaminated by iodine-sensitive spots both above and below. These fractions were rotary evaporated to give 2.52 g of a semisolid paste. An I.R. spectrum showed absorptions at 1583 and 1567 cm−1. The impure product as used directly in the next reaction step.

2-Chloro-5-(2,2,2-trifluoroethoxy-(5'-chloro)tricyclo [3.3.1.1$^{3,7}$]dec-2-ylidenemethy)phenol Sodium hydride (60% dispersion, 240 mg.; 6.0 mmol) was washed with hexanes three time under argon. DMF, 17 mL, was added. The ice cooled slurry was treated dropwise with ethanethiol (450 microliters; 6 mmol) from a syringe. After warming this solution to room temperature, the evolution of hydrogen was complete. The solution was added by pipette (argon) to the product of the preceding reaction. The mixture was stirred and heated under argon at 120° C. for 1.25 hours. The cooled reaction mixture was partitioned in 70 mL 40% hexanes in ethyl acetate against 70 mL of 1M ammonium chloride solution. After washing again with water, 3 times, the organic layer was dried over sodium sulfate. The solvents were stripped and the residue was chromatographed on aluminum oxide using 50:50 ethyl acetate/hexanes, followed by ethyl acetate and finally by 2% methanol in ethyl acetate. The lower Rf product was obtained from 2 fractions as an amber gum weighing 0.58 g. The PMR spectrum showed impurities, but the major absorptions for the desired product were found at:

$^1$H NMR (400 MHz-$CDCl_3$): δ 1.56–2.21 (m, 13H); 2.73(s, 1H); 3.45(s, 1H); 3.70–3.76, (m, 2H-$\underline{CH}_2CF_3$); 5.62 (br. s., 1H); 6.78–7.33(m, 3H).

The product was found to be sufficiently pure to be converted to the cyanoethyl phosphate diester enol ether as follows:

1.2 g of the phenol (2.95 mol) in 12 mL dry THF was treated with 535 microliters of triethylamine. The mixture was stirred at 0° C. under argon while 2-chloro-2-oxo-1,3, 2-dioxaphospholane (326 microliters, 3.54 mmol) was added dropwise by syringe. The resulting suspension was stirred at room temperature for 3 hours and filtered under argon. The precipitate was washed with 3×10 mL of 3:1 dry THF/dry ether. The filtrate was pumped to an amber oil which was dissolved in 7 mL anhydrous DMF. The solution was treated with 60 mg dry NaCN and stirred overnight at room temperature. The DMF was removed in vacuo at 50° C. to provide the orange, gummy cyanoethylphosphate diester which was used directly in the next step.

Disodium 3-(4-(2,2,2-trifluoroethoxy)spiro{1,2-dioxetane-3,2'-(5'-chloro)tricyclo [3.3.1.1$^{3,7}$]decan}-4-yl)phenyl phosphate The phosphate diester was placed in a tube and wetted down with anhydrous methanol, 4 mL. Chloroform, 40 mL, was added to obtain a clear solution. A solution of tetraphenylporphine (TPP), 6 milligrams in 3 mL chloroform, was then added to yield a pink-purple reaction mixture. The solution was cooled in an ice bath while sparging with oxygen through a Pasteur pipette for 5 minutes. The gas flow was continued while the solution was irradiated with a 400 watt sodium vapor lamp which had been filtered with a 3.0 mil thickness of DuPont Kapton film. After 1.5 hours, a small sample was blown down and dissolved in water which contained NaOH. Analytical HPLC of this basified sample, under conditions described above, indicated that the major product eluted at 12.6 minutes. Collection of this peak, dilution into pH 10 aqueous diethanolamine buffer, and addition of excess alkaline phosphatase gave a burst of light lasting 3 minutes. The reaction was stripped of solvents and pumped to yield a dark red gum. This was dissolved in 10 mL methanol, and treated with 690 microliters of 4.37M sodium methoxide in methanol. After 40 minutes at room temperature, half of the methanol was removed on the rotary evaporator. Water, 60 mL, was added and the solution was filtered through 0.45 micron nylon filters, rinsing with another 20 mL of water. This solution was preparatively chromatographed on a one inch PLRP-S column (Polymer Laboratories) using an acetonitrile/water gradient. The product peak was shaved on the front and in the back, collecting only the middle cut. This eluant was freeze dried to obtain 605 milligrams of the product as a white solid.

$^1$H NMR (400 MHZ-D$_2$O): δ 0.82–2.22 (m, 1H): 2.38 (br. s., 1H); 3.05 (s, 1H); 3.86 (br. m., 2H); 7.10–7.71 (m, 3H)

Wittig-Horner-Emmons Synthetic Pathway

An alternate methodology for the synthesis of fluoroalkoxy 1,2-dioxetanes of the invention involves the Wittig-Horner-Emmons condensation of α-fluoroalkoxy arylmethane phosphonate esters with 2-adamantanone or substituted 2-adamantanones. Konenigkramer and Zimmer (J. Org. Chem., 45, 3994–3998, 1980), describe the reaction of benzaldehyde with triethylphosphite and chloromethylsilane to give diethyl 1-trimethylsiloxy-1-phenylmethanephosphonate. Creary and Underiner (J. Org. Chem., 50, 2165–2170, 1985) further detail the conversion of the related α-trimethylsiloxy substituted-phenylmethanephosphonate esters to the corresponding α-fluoroalkoxy phosphonates via the α-mesyloxy or α-trifloxy derivatives. Using this route with trifluoroethanol, one of the possible fluorinated alcohols, 4-chloro-3-methoxybenzaldehyde yields diethyl 1-(2,2,2-trifluoroethoxy)-1-(4-chloro-3-methoxyphenyl)methane phosphonate. This is then condensed with 5-chloro-2-adamantanone to yield an enol ether which is subsequently converted to an enzyme triggerable dioxetane in accordance with the examples provided.

One of skill in the art would also be aware that a sodium salt of the appropriate alcohol or phenol could be reacted with the benzyl halide derivative of the aldehyde in the resence of assisting silver salts to give a haloalkyl or haloaryl acetal which could then be utilized to synthesize other arylmethyl phosphonates and enol ethers by Wittig Horner Emmons reaction.

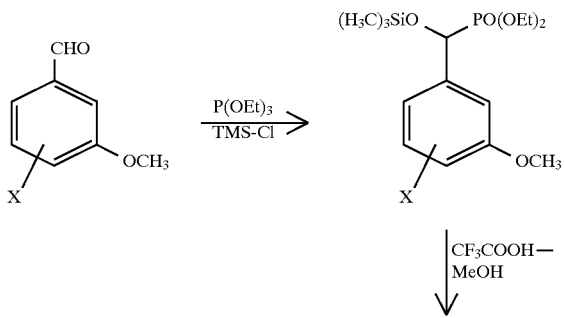

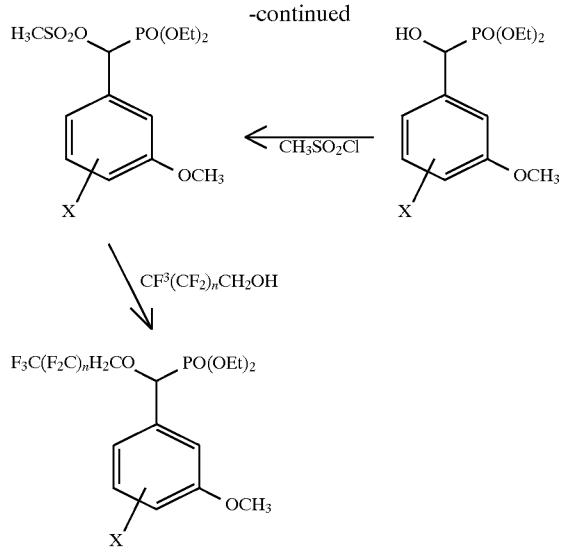

The phosphonate ester shown is synthesized by the following method:

Synthesis of 4-Chloro-3-methoxyphenyl(2,2,2-trifluoroethoxy)diethyl-phosphonate

The 2,2,2-trifluoroethoxydiethylphosphonate (compound 3, below) was synthesized from bis(2,2,2-trifluoroethyl)4-chloro-3-methoxybenzaldehyde acetal (compound 2, below) which was obtained from the 4-chloro-3-methoxybenzaldehyde dichloroacetal (compound 1, below)

4-Chloro-3-methoxybenzaldehyde dichloroacetal (1)

4-Chloro-3-methoxybenzaldehyde (1.5 g, 8.8 mmol) was added to PCI$_5$ (2.45 g, 11.8 mmol) under argon and was stirred for 15 min. while heat evolved from the liquefied mixture. Methylene chloride (3 ml) was added and the solution was stirred overnight at room temperature; TLC analysis indicated a trace of UV activity from the starting benzaldehyde remained. Additional CH$_2$Cl$_2$ (15 ml) and saturated NaHCO$_3$ solution (40 ml) were added and the solution was stirred for 1 hr at room temperature to quench the reaction. The reaction mixture was partitioned between CH$_2$Cl$_2$ and water, the aqueous layer was washed once with CH$_2$Cl$_2$ and the combined organic layers were dried over Na$_2$SO$_4$. The product was recovered after evaporating the solvent under pressure and pumping to dryness on high vacuum. Purification of the oil on silica gel, eluting with 4% EtOAc/hexanes, yielded 1.73 g (87%) of dichloroacetal 1 as a light yellow oil.

$^1$H NMR (CDCl$_3$, ppm): 3.94 (3H, s); 6.65 (1H, s); 7.03 (1H, dd, J=2 Hz, 8 Hz); 7.15 (1H, d, J=2 Hz); 7.35 (1H, d, J=8 Hz)

Bis(2,2,2-trifluoroethyl)4-chloro-3-methoxybenzaldehyde acetal (2)

Dichloroacetal 1 (835 mg, 3.7 mmol) was dissolved in 2,2,2-trifluoroethanol (4 ml) and cooled to 0° C. Sodium hydride (429 mg, 60% in oil, 10.7 mmol) was added in portions to the solution at low temperature to generate sodium 2,2,2-trifluoroethanoate in situ. After adding anhydrous silver carbonate (2.1 g, 7.6 mmol), the reaction mixture was heated at 80° C. for 1 hr to effect acetylation. Upon cooling, water and EtOAc were added with stirring and the solution was filtered through a cotton plug to remove solids. The solids were rinsed well with EtOAc and the resulting organic solution was partitioned between EtOAc and water. The EtOAc solution was dried over Na$_2$SO$_4$, decanted and evaporated to an oil which was purified on a silica gel column (0–1% EtOAc/hexanes) to yield 1.13 g (86%) of trifluoroethylacetal 2 as an oil. A small amount of product (42 mg) was further purified on a prep TLC plate for spectral analysis.

IR (CHCl$_3$, nm$^{-1}$): 2940, 1590, 1580, 1482, 1457, 1405, 1267, 1164, 1064, 1029, 964, 870

$^1$H NMR (CDCl$_3$, ppm): 3.83–3.94 (4H, m); 3.90 (3H, s); 5,82 (1H, s); 7.00–7.02 (2H, m); 7.39 (1H, d, J=8.5 Hz)

4-Chloro-3-methoxyhenyl(2,2,2-trifluoroethoxy) diethylphosphonate (3)

Triethyl phosphate (530 μl, 3.1 mmol) and boron trifluoride etherate (420 μl, 3.4 mmol) were added, at 0° C. under argon, to trifluoroacetal 2 (1.09 g, 3.1 mmol) dissolved in CH$_2$Cl$_2$ (10 ml). The reaction mixture was allowed to warm to room temperature with stirring over 3 hrs. During this time additional triethyl phosphite (100 μl, 0.6 mmol) and boron trifluoride etherate (250 μl, 2.0 mmol) were added to complete the reaction. The solution was partitioned between CH$_2$Cl$_2$ and dilute brine and the aqueous layer was washed well with CH$_2$Cl$_2$. The combined organic layers were then washed with saturated NaHCO$_3$, dried over Na$_2$SO$_4$, decanted and evaporated. The colorless oil was purified on a silica gel column flushed with hexanes and eluted with 0–50% EtOAc/hexanes to give 752 mg (62%) of phosphonate 3 as a clear oil. A small sample (47 mg) of the oil was further purified on a prep TLC plate for spectral analysis.

IR (CHCl$_3$, nm$^{-1}$); 2990, 1590, 15981, 1484, 1460, 1410, 1277, 1255, 1165, 1113, 1051, 1030, 970

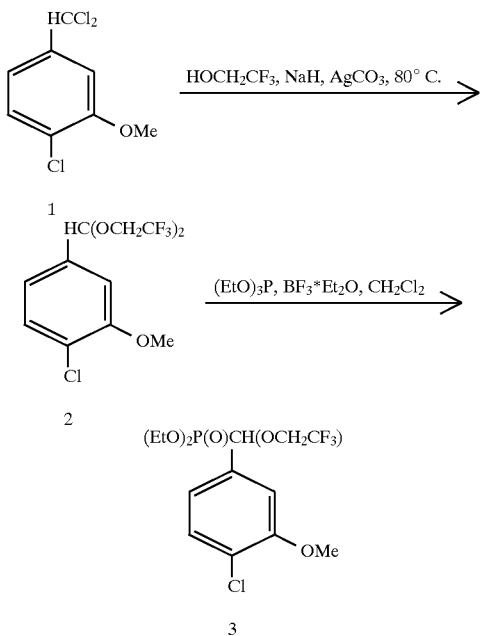

We performed comparisons of chemiluminescence half-lives (t½) for the following dioxetanes:

Determination of the Chemiluminescence Half-Life of Dephosphorylated Dioxetane

A 1 mL aliquot of each dioxetane (0.004 mM) was equilibrated to 30° C. in 0.1M diethanolamine, 1 mM MgCl$_2$, pH 10. Alkaline phosphatase (at final concentration of 1.05×10$^{-9}$M) was added to the test tube and the chemiluminescent signal kinetics was measured in a Turner TD-20E luminometer for 10 to 20 minutes. The half-life was calculated from the plot of log RLU versus time. For TFE and TFE-ADP-Star, the chemiluminescent half-life was also determined in the presence of Sapphire II enhancer (in 0.1M diethanolamine, 1 mM MgCl$_2$, 10% polyvinylbenzyltributyl ammonium chloride at 1 mg/mL). The results are listed in TABLE I:

TABLE I

| DIOXETANE | T1/2 (MINUTES) |
|---|---|
| TFE-ADP-Star | 2.0 |
| TFE | 0.9 |
| ADP-Star | 2.7 |
| CDP-Star | 1.2 |
| CSPD | 0.6 |
| TFE/Sapphire II | 15.5 |
| TFE-ADP-Star/Sapphire II | 5.0 |

Determination of the Peak Light Intensity of Dephosphorylated Dioxetanes

A 0.5 mL aliquot of dioxetane (0.004 mM) was equilibrated to 30° C. in 0.1M diethanolamine, 1 mM MgCl$_2$, pH 10. Alkaline phosphatase (final concentration of 1.05×10$^{-9}$M) was added to the tube and the chemiluminescent signal was measured in a Turner TD-20E luminometer for 10 to 20 minutes. The peak light intensity was recorded and is shown in TABLE II

TABLE II

| DIOXETANE | PEAK INTENSITY (RLU) |
|---|---|
| TFE-ADP-Star | 390 |
| TFE | 282 |
| ADP-Star | 682 |
| CDP-Star | 863 |
| CSPD | 200 |

Detection of Biotinylated pBR322(35 mer) on Nylon Membrane

Serial dilutions of biotinylated pBR322(35 mer) were spotted onto strips of Tropilon-Plus nylon membrane. Spots correspond to 210 pg, 70 pg, 23.3 pg, 7.7 pg, 2.6 pg, 0.86 pg, 0.29 pg, 0.10 pg, 32.0 fg, 10.7 fg, 3.6 fg and 1.2 fg of biotinylated pBR322(35 mer). After spotting, the DNA was cross-linked to the membrane by UV fixation, the membranes were blocked with 0.2% I-Block, 5% sodium dodecyl sulfate (SDS) in phosphate buffered saline(PBS) (Blocking Buffer I), incubated with a 1–5000 dilution of Avidx-AP in Blocking Buffer I for 30 minutes, washed twice with 5% SDS in PBS for 5 minutes, rinsed twice with Assay Buffer, incubated for 5 minutes in 0.25 mM dioxetane phosphate in Assay Buffer and exposed to X-ray film for 5 minutes. The membrane strips incubated with CSPD, and TFE were rinsed with 0.1M diethanolamine, 1 mM MgCl$_2$, pH 9.5 and those incubated with CDP-Star, and TFE-ADP-Star were rinsed with the same buffer at pH 9.0. The Assay Buffer for CSPD and TFE was 0.1M diethanolamine, 1 mM MgCl$_2$, pH 9.5 and for CD-Star, and TFE-ADP-Star was the same buffer at pH 9.0. The detection sensitivities, obtained in a 5 minute exposure are listed in TABLE III.

TABLE III

| DIOXETANE | DNA CONC. (PICOGRAMS) |
|---|---|
| TFE-ADP-Star | 0.0107 |
| TFE | 7.7 |
| CDP-Star | 0.86 |
| CSPD | 23.3 |

The comparison of the experimental data points out that the presence of the haloalkoxy substituent on AMPPD (TFE)

reduces the chemiluminescence half-life in a buffer solution (t½ for AMPPD is 2.1 min, t½ for TFE is 0.9 min.), however, in the presence of enhancers the t½ increases to 15 min. These dioxetanes are particularly commercially useful when enhanced by either a solution enhancer (such as TBQ, TB or in a CTAB-fluorescein as in LumiPhos 430) or a surface (such as nylon membrane). However, TFE without the electron active substituent on the phenyl ring does not provide any advantages. Furthermore, even by itself in a buffer, the CSPD half-life is shorter than TFE. The peak intensity data in TABLE II shows the comparison of the chemiluminescent signal intensity or the relative emission efficiencies. The results clearly indicate that TFE-ADP-Star generates a higher intensity signal. Superior conventional utilities are offered by TFE-ADP-Star.

TABLE III shows the comparison of these dioxetanes in a blotting application for the detection of DNA on a nylon membrane. This data shows an unexpected advantage of TFE-ADP-Star, which does not exist in TFE or other compounds. TFE-ADP-Star detects close to one thousand times less DNA than TFE. In this particular application, TFE-ADP-Star is also more sensitive than CDP-Star.

As demonstrated above, the dioxetanes of this invention can be used to detect the presence of an enzyme in a sample, as well as reporter molecule to detect the presence of a nucleic acid sequence. Generally, there are a wide variety of assays and assay formats which exist which can make use of the dioxetanes, all employing visually detectable chemiluminescence of the deprotected oxyanion decomposition to indicate the presence and/or concentration of a particular substance in a sample.

For example, when using this invention to detect an enzyme in a sample, the sample is contacted with a dioxetane bearing a group capable of being cleaved by the enzyme being detected. The enzyme cleaves the dioxetane's enzyme cleavable group to form a negatively charged substituent (e.g., an oxygen anion) bonded to the dioxetane. This negatively charged substituent in turn destabilizes the dioxetane, causing the dioxetane to decompose to form a fluorescent chromophore group that emits light energy. It is this chromophore group that is detected as an indication of the presence of the enzyme. By measuring the intensity of luminescence, the concentration of the enzyme in the sample can also be determined.

The above-described dioxetanes can be used in any reporter molecule based assay with an acceptable environment. Examples of such assays include immunoassays to detect antibodies or antigens, e.g., δ- or β-hCG; enzyme assays; chemical assays to detect, e.g., potassium or sodium ions; and nucleic acid assays to detect, e.g., viruses (e.g., HTLV III or cytomegalovirus, or bacteria (e.g., *E. Coli*), and certain cell functions (e.g., receptor binding cites).

When the detectable substance is an antibody, antigen, or nucleic acid, the enzyme capable of cleaving the enzyme cleavable group of the dioxetane is preferably bonded to a substance having a specific affinity for the detectable substance (i.e., a substance that binds specifically to the detectable substance), e.g., an antigen, an antibody, or nucleic acid probe. Conventional methods, e.g., carbodiimide coupling, are used to bond the enzyme to the specific affinity substance; bonding is preferably through an amide linkage.

In general, assays are performed as follows. A sample suspected of containing a detectable substance is contacted with a buffered solution containing an enzyme bonded to a substance having a specific affinity for the detectable substance. The resulting solution is incubated to allow the detectable substance to bind to the specific affinity portion of the specific affinity-enzyme compound. Excess specific affinity-enzyme compound is washed away, and a dioxetane having a group cleavable by the enzyme portion of the specific affinity-enzyme compound is added. The enzyme cleaves the enzyme cleavable group, causing the dioxetane to decompose into two carbonyl compounds (e.g., an ester, a ketone or an aldehyde). The chromophore to which the enzyme cleavable group had been bonded is thus excited and luminesces. Luminescence is detected (using, e.g., a cuvette, or light-sensitive film in a camera luminometer, or a photoelectric cell or photomultiplier tube), an indication of the presence of the detectable substance in the same. Luminescence intensity is measured to determine the concentration of the substance.

In solid state assays, the specific membranes of U.S. Pat. No. 5,336,596 incorporated herein-by-reference, can be advantageously employed. The use of other membranes, as well as other solid phases in an assay, may be improved by blocking non-specific binding to the solid phase matrix by pretreatment with non-specific proteins such as BSA or gelatin. Non-specific binding can also be blocked by application, to the membranes, of a variety of polymeric quaternary onium salts, such as are disclosed in U.S. Pat. No. 5,326,882.

In the alternative, as fully set forth in U.S. Pat. No. 4,978,614 and pending U.S. patent application Ser. No. 08/031,471, one may use polymeric quaternary onium (phosphonium, sulfonium and ammonium) quaternary salts. The disclosure of these enhancement agents which can be used alone, or in conjunction with surfactants, is incorporated herein by reference. It is believed that these enhancement agents, in an aqueous environment, sequester the hydrophobic deprotected oxyanion, substantially excluding water from the microenvironment in which decomposition, and chemiluminescence occurs. As water tends to "quench" chemiluminescence, its exclusion by the hydrophobic enhancement agents can dramatically improve chemiluminescence characteristics, as demonstrated in the above-experiments.

The dioxetanes of this invention, and their application and preparation have been described both generically, and by specific example. The examples are not intended as limiting. Other substituent identities, characteristics and assays will occur to those of ordinary skill in the art, without the exercise of inventive faculty. Such modifications remain within the scope of the invention, unless excluded by the express recitation of the claims advanced below.

What is claimed is:

1. A kit comprising:

(a) a dioxetane of the formula

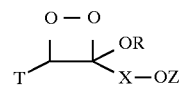

wherein T is spiroadamantyl, unsubstituted or substituted at one or both bridgehead carbons, said substituents being independently selected from the group consisting of a hydroxyl group, F, Cl, an unsubstituted straight or branched chain alkyl group of 1–6 carbon atoms, an alkyl group of 1–6 carbon atoms mono-di-or tri-substituted with a hydroxy or 1–3 halogen atoms, a phenyl group, a cyano group and an amide group;

wherein X is phenyl or naphthyl, bearing 1–3 electron active substituents, each of said electron active substituents being independently selected from the group consisting of Cl, F, alkoxy, aryloxy, trialkylammonium, alkylamido, arylamido, arylcarbamoyl, alkylcarbamoyl, cyano, nitro, ester, alkyl-or arylsulfonamido, trifluoromethyl, aryl, alkyl, trialkyl-triaryl-or alkylarylsilyl, alkyl-or arylamidosulfonyl, alkyl-or arylsulfonyl and alkyl- or arylthioether, wherein, in each case, each alkyl or aryl moiety is comprised of 1–12 carbon atoms;

wherein Z is an enzyme cleavable moiety, H or $E_3Si$, wherein each E is independently H, alkyl, aryl, or aralkyl of 1–12 carbon atoms, and wherein R is alkyl, aryl, aralkyl or cycloalkyl of 1–20 carbon atoms, which may contain 1–2 heteroatoms selected from the group consisting of P, N, S and O, wherein R bears at least one halogen substituent; and (b) a triggering agent which removes Z when admixed with said dioxetane in an aqueous environment.

2. The kit of claim 1, wherein Z is enzyme cleavable, and said triggering agent is an enzyme which cleaves said group Z.

3. The kit of claim 1, wherein Z is triggerable by a non-enzymatic chemical and said triggering agent is a base.

* * * * *